United States Patent [19]
Oshima et al.

[11] 4,083,496
[45] Apr. 11, 1978

[54] ATOMIZER

[75] Inventors: Isao Oshima, Kobe; Akira Yokogi, Ibaraki, both of Japan

[73] Assignee: Takeda Chemical Industries, Ltd., Osaka, Japan

[21] Appl. No.: 736,188

[22] Filed: Oct. 27, 1976

[30] Foreign Application Priority Data

Oct. 28, 1975 Japan .................. 50-147264[U]
Nov. 10, 1975 Japan .................. 50-153199[U]

[51] Int. Cl.² ......................................... B05B 7/24
[52] U.S. Cl. .............................. 239/327; 239/350
[58] Field of Search ............ 239/327, 350, 356, 363; 222/209, 211

[56] References Cited

U.S. PATENT DOCUMENTS

| | | | |
|---|---|---|---|
| 423,198 | 3/1890 | Windolph | 239/327 |
| 2,573,731 | 11/1951 | Ryberg et al. | 239/327 |
| 2,796,295 | 6/1957 | McKinnon | 239/356 |
| 3,341,130 | 9/1967 | Weber | 239/327 |
| 3,367,330 | 2/1968 | Sierpin | 239/356 X |
| 3,369,713 | 2/1968 | Godschalk, Jr. | 239/327 X |

FOREIGN PATENT DOCUMENTS

| | | | |
|---|---|---|---|
| 527,563 | 10/1921 | France | 239/356 |
| 680,855 | 10/1952 | United Kingdom | 239/356 |

*Primary Examiner*—John J. Love
*Attorney, Agent, or Firm*—Sughrue, Rothwell, Mion, Zinn and Macpeak

[57] ABSTRACT

An atomizer for spraying a liquid medium into minute particles which comprises an outer container, a nozzle assembly including a hollow nozzle member, having a substantially elongated passage defined therein, and a body portion through which the nozzle assembly is coupled to the outer container. An inner container including a tube portion and a container portion in which a predetermined amount of liquid medium to be sprayed is contained is utilized independently of the outer container. This inner container is installed within the atomizer while the tube portion extends through the passage with one end disposed adjacent the nozzle and the other end coupled to the container portion. By the application of a grip to the outer container, the liquid medium can be drawn upwards through the tube portion onto the nozzle through which it is atomized.

2 Claims, 9 Drawing Figures

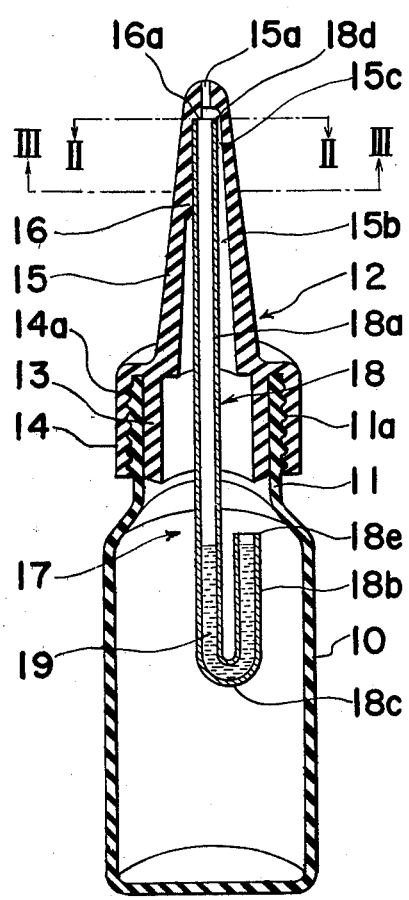
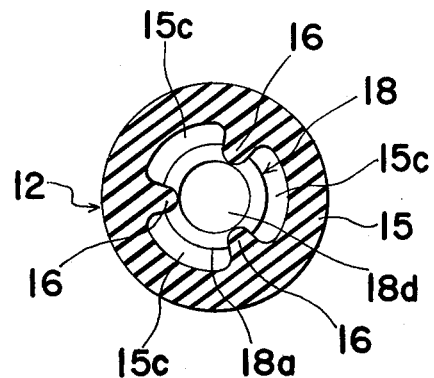
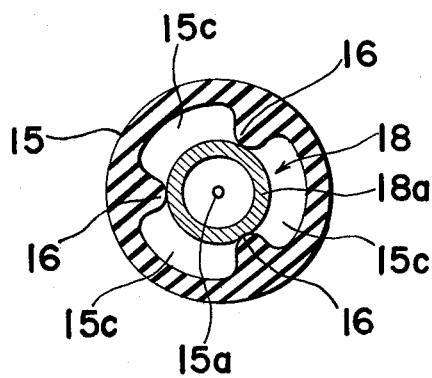
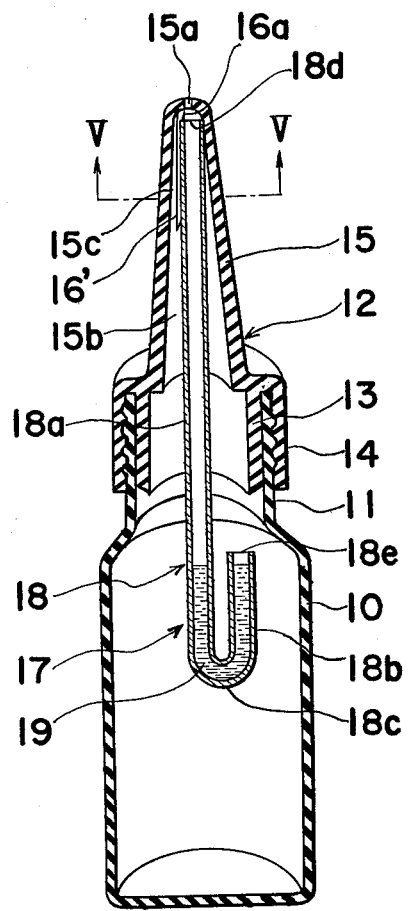

ATOMIZER

The present invention generally relates to an atomizer and, more particularly, to a compact, portable atomizer of a type utilizable in combination with a replaceable tubular container containing therein a predetermined amount of liquid medium to be atomized at one time.

Various types of atomizer are now commercially available and so many in application. So far as a compact atomizer or applicator for injecting liquid medium, for example, a medicinal solution, in the form of minute particles into the nasal canal of a patient suffering from a particular disease is involved, there is known an atomizer or applicator which comprises a bottle-like container filled with medicinal solution and having an opening defined at the mouth thereof, and a nozzle assembly including a hollow guide tube and a substantially elongated nozzle member having a passage defined therein and extending completely through the length of the nozzle member. While the guide tube has one end inserted into the passage in the nozzle member, the nozzle member is formed with a plurality of parallel ribs extending in parallel to the longitudinal axis of the passage and in equally spaced relation to each other and radially inwardly protruding from the nozzle member into the passage thereby retaining that end of the guide tube in position within the passage. One open end of the passage, which is adjacent that end of the guide tube inserted into the passage, serves as a nozzle orifice through which the medicinal solution is atomized in a manner as will be described later.

The nozzle assembly is mounted on the mouth of the bottle-like container with the other end of the nozzle member tightly sealing the opening at the mouth of the container, while the other end of the guide tube extends into the medicinal solution within the container and terminates adjacent the bottom of said container.

In this conventional atomizer of the construction as hereinabove described, that end of the guide tube adjacent the nozzle orifice is so spaced from and so located inwardly of the nozzle orifice that, when a single grip is applied to the body of the container, a part of the air contained within the container above the surface level of the medicinal solution is expelled towards the outside of the atomizer through the nozzle orifice, first upwardly flowing through the passage and then through interstices defined between each adjacent pair of the parallel ribs, creating a negative pressure within the guide tube and at the same time the remaining air presses the surface level of the solution. By the effect of this positive pressure so developed, a portion of the medicinal solution within the container is extruded upwards through the guide tube and then atomized through the nozzle orifice.

While the conventional atomizer of the construction described above is satisfactory in respect of its performance, the amount of medicinal solution atomized or to be atomized tends to vary depending upon the amount of the grip applied to the body of the container. While the grip varies from person and person and, moreover, the grip of the same person varies from time to time, the conventional atomizer is not suited for atomizing a predetermined amount of liquid medium into minute particles irrespective of the amount of grip applied.

If an atomizer is so constructed that a single grip applied to the body of the container can result in atomization of a predetermined amount of liquid medium, the atomizer so constructed would be used in association with any other medicinal solution or suspension of the nature a dosage of which is required to be strictly controlled.

Accordingly, the present invention has been developed in view to providing an improved atomizer of a type which can atomize a predetermined amount of liquid medium by the application of a single grip to the body of the bottle-like container.

According to the present invention, an essential feature resides in the use of a tubular container independently of the bottle-like container which is, according to the prior art, used to contain liquid medium. In one preferred embodiment of the present invention, the tubular container is in the form of a substantially J-shaped tube having one end removably inserted into the passage in the nozzle member and positioned adjacent the nozzle orifice and the other end upwardly opening within the bottle-like container, a substantially U-shaped portion of the J-shaped tube being used to contain a predetermined amount of liquid medium to be atomized at one time.

These and other objects and features of the present invention will become apparent from the following description taken in conjunction with preferred embodiments thereof with reference to the accompanying drawings, in which:

FIG. 1 is a perspective view of an atomizer, shown in section, according to one preferred embodiment of the present invention;

FIG. 2 is a cross sectional view taken along the line II—II in FIG. 1;

FIG. 3 is a cross sectional view taken along the line III—III in FIG. 1;

FIG. 4 is a view similar to FIG. 1, showing another preferred embodiment of the present invention;

Before the description of the present invention proceeds, it is to be noted that like parts are designated by like reference numerals throughout the accompanying drawings.

Figure 5:
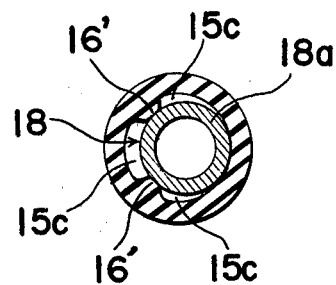
FIG. 5 is a cross sectional view taken along the line V—V in FIG. 4.

Referring now to FIGS. 1 to 3, an atomizer is shown to comprise a bottle 10 made of elastically deformable material, such as a flexible plastic, and formed with a cylindrical mouth 11 having a helical thread 11a defined on the outer peripheral surface thereof.

The illustrated atomizer further comprises a nozzle assembly, generally indicated by 12, of one-piece construction made of a plastic material. The nozzle assembly 12 is shown to include a cylindrical body of double-walled construction having inner and outer cylindrical walls 13 and 14 spaced from each other a distance corresponding to the thickness of the wall defining the bottle mouth 11. These inner and outer walls 13 and 14 are integrally connected to each other at one end thereof which are in turn integrally connected with one end of an outwardly tapered nozzle member 15 which has a nozzle 15a, defined at the tip of said member 15 remote from the double-walled cylindrical body, and a passage 15b in communication with the nozzle 15a. While the inner wall 13 has an outer diameter substantially equal to or approximating to the inner diameter of the mouth 11, the outer wall 14 has a helical thread 14a defined on the inner peripheral surface thereof in complemental relation to the helical thread 11a on the mouth 11 whereby the nozzle assembly 12 can be mounted on the bottle mouth 11 with the inner and outer walls 13 and 14 respectively situated innerwardly and outerwardly of the mouth 11 as shown in FIG. 1.

The nozzle member 15 is formed with a plurality of, for example, three, parallel ribs 16 extending in parallel relation to the longitudinal axis of the nozzle member 15 and radially inwardly protruding into the passage 15b in equally spaced relation with each other about the longitudinal axis of the nozzle member 15, as substantially shown in FIGS. 2 and 3, at a position adjacent the nozzle 15a. Each of these ribs 16 is indented at 16a, an upper portion thereof adjacent the nozzle 15a further radially inwardly protruding beyond the remaining portion of the same rib 16, for the purpose as will become clear from the subsequent description.

A tubular inner container, generally indicated by 17, is shown to be comprised of a substantially J-shaped tube 18 made of glass or a plastic material and having a long straight portion 18a, a short straight portion 18b and a substantially U-shaped portion 18c, said U-shaped portion 18c having its opposed ends integrally connected to the long and short straight portions 18a and 18c. So far illustrated, the openings at respective free ends of the long and short straight portions 18a and 18b of the J-shaped tube 18, which are remote from the U-shaped portion 18c, face in the same direction and are positioned spaced apart from each other. The tubular inner container 17 of the one-piece construction as described above is installed in a manner as shown in FIG. 1 and as will subsequently be described only when the atomizer according to the present invention is put into use. However, prior to the installation of the inner container 17 in the manner as shown, the openings 18d and 18e at the respective free ends of the long and short straight portions 18a and 18b are, after a predetermined amount of liquid medium to be atomized or sprayed is filled in the interior of the tube 18, closed by any suitable closures, for example, plastic caps or rubber closures, or sealed by heat. It is to be noted that the amount of the liquid medium to be filled in the tube 18 should be so selected that, when the tube 18 is held in upright position with the openings 18d and 18e facing upwards as substantially shown in FIG. 1 and the liquid medium tending to remain stationary due to its inherent inertia subsequently becomes stationary as indicated by 19 in FIG. 1, the surface level of a portion of the liquid medium 19 within the short straight portion 18b is located substantially at or below the level of the opening 18e which is positioned below the level of the opening 18d, the remaining portion of the liquid medium 19 filling the U-shaped portion 18c and one end portion of the long straight portion 18a adjacent said U-shaped portion 18c. In other words, the amount of the liquid medium 19 is so selected that it will not overflow from the opening 18e even when the tube 18 is held in the upright position.

While the tubular inner container 17 in the embodiment of FIGS. 1 to 3 is constructed as hereinbefore described, the tubular inner container 17 is installed in such a manner that the free end portion 18d of the long straight portion 18a of the tube 18 is inserted into the passage 15b with its end face engaging the steps 16a in the respective ribs 16 and spaced a predetermined distance from the nozzle 15a. By so doing, the tube 17 can be firmly retained in position with no substantial possibility of arbitrary separation thereof from the nozzle member 15.

When the inner container 17 is so installed, it will readily be seen that an upper portion of the passage 15b adjacent the nozzle 15a and surrounded by the parallel ribs 16 is, as best shown in FIGS. 2 and 3, constituted by interstices 15c extendng in parallel relation to each other and defined between each adjacent pair of the parallel ribs 16, the remaining portion of said passage 15b being in communication with the nozzle 15a through said interstices 15c.

In the assembled condition, as shown in FIG. 1, with the cylindrical body 13, 14 tightly mounted on the mouth 11 of the bottle 10, the tube 18 extends downwards into the interior of the bottle 10 with the end portion of the long straight portion 18a adjacent the U-shaped portion 18c situated therein together with the U-shaped and short straight portions 18c and 18b.

It is to be noted that, in the embodiment shown in FIGS. 1 to 3, the employment has been described of the three parallel ribs 16. However, the number of the ribs 16 is not always limited to three or more, but may be one or more. Although the long straight portion 18a can be aligned with the longitudinal axis of either or both of the nozzle 15a and the passage 15b, such as shown in FIG. 1, if the number of the ribs 16 employed is three or more, the employment of one rib will not bring any substantial reduction in performance of the atomizer according to the present invention. An example wherein two parallel ribs are employed is illustrated in FIGS. 4 and 5, which ribs are generally indicated by 16'.

As can readily be seen from FIG. 5, the free end portion of the long straight portion 18a of the tube 18 is laterally displaced with respect to the longitudinal axis of the passage 15b and, therefore, relative to the longitudinal axis of the nozzle 15a.

The atomizer according to any one of the embodiments of FIGS. 1 to 3 and FIGS. 4 and 5 functions in the following manner. Starting from the condition as shown in 1 or 4, if a grip is applied to the body of the bottle 10, air contained within the bottle 10 is forced to discharge to the atmosphere through the nozzle 15a, first flowing upwards through the passage 15b and then through the interstices 15c. During the flow of the air through the interstices 15c past the outer peripheral edge of the free end of the long straight portion 18a, a negative pressure is developed within the long straight portion 18a of the tube 18 above the surface level of the liquid medium 19. At the same time, the air presses the surface level of the solution. By the effect of mainly this positive pressure so developed, the liquid medium within the tube 18 is upwardly extruded through the long straight portion 18a and then discharged through the nozzle 15a so adjoining a stream of air passing through the passage 15b onto the nozzle 15a that the liquid medium discharged can be atomized in the form of minute particles. The whole amount of the liquid medium 19 within the tube 18 is thus atomized by the application of the grip to the body of the bottle 10.

Where replacement of the used tube 18 with a fresh one is desired, what is required is to separate the nozzle assembly 12 from the bottle 10, then to remove the used tube 18 from the nozzle assembly and finally to insert the fresh tube in the manner as hereinbefore described.

Figure 6:
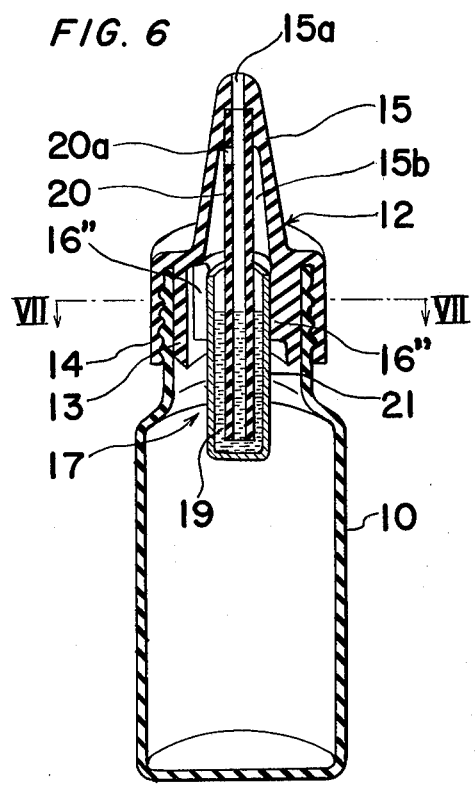
FIG. 6 is a view similar to FIG. 1, showing a further preferred embodiment of the present invention.
Figure 7:
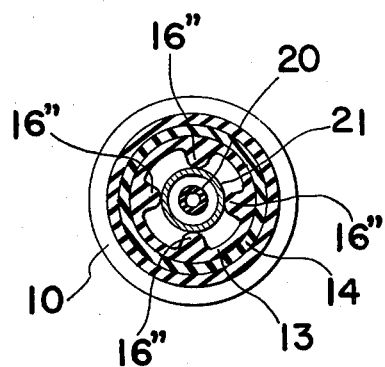
FIG. 7 is a cross sectional view taken along the line VII—VII in FIG. 6.

In the embodiment shown in FIGS. 6 and 7, the tubular inner container 17 is shown to be comprised of a tube 20, having one end inserted into, or otherwise rigidly secured to, the wall of the nozzle member 15 in alignment with the nozzle 15a, and a substantially cylindrical container 21. A plurality of, for example, four, retaining ribs 16", which are functional equivalents of the parallel ribs 16 employed in the embodiment of FIG. 1, are defined on the inner peripheral surface of the inner wall 13 and radially inwardly extend therefrom whereby, when the cylindrical container 21 is inserted into the nozzle assembly 12, the container 21 can be retained in position with an open end thereof retained by the radially inwardly extending parallel ribs 16" in a manner as best shown in FIG. 7 while the other end portion of the tube 20 extends into the interior of the container 21 as best shown in FIG. 6.

The tube 21 has a hole or orifice 20a defined therein at a position adjacent the nozzle 15a, through which orifice 20a the air flows towards the nozzle 15a past the interstices defined between each adjacent pair of the parallel ribs 16" when the grip is applied to the body of the bottle 10. As hereinbefore described in connection with the operation of the atomizer according to any one of the embodiments of FIGS. 1 to 5, the flow of the air through the orifice 20a results in development of the positive pressure on the surface level of medium 19 near the opening end 18e in the container necessary to draw the liquid medium upwards from the container 21 through the tube 20. In this way, the liquid medium 19 can be sprayed or atomized to the atmosphere through the nozzle 15a.

Figure 8:
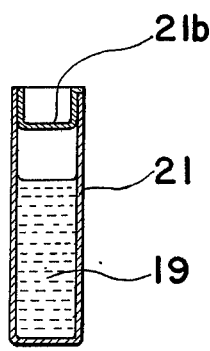
FIGS. 8 and 9 are longitudinal sectional views showing respective variations of an inner container for containing a predetermined amount of liquid medium to be atomized, which may be advantageously used with the atomizer of the construction shown in FIG. 6.
Figure 9:
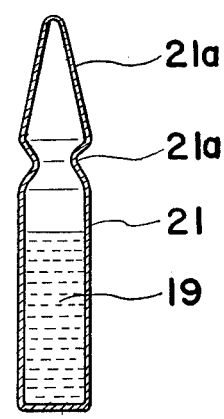

It is to be noted that the container 21 is, when not installed in the manner as shown in FIG. 6, closed at its opposed ends. Only one of the opposed ends of the container 21 is opened when the container 21 is to be installed in the manner as shown. For this purpose, the container 21 may be in the form of an ampoule as shown in FIG. 9 of a type having a head portion 21a separable from the body of the container by breaking at a neck 21a in any known manner. Alternatively, the container 21 may be of a type having one end closed and the other end adapted to be closed by an insert 21b, or any other suitable closure member, as shown in FIG. 8.

Although the present invention has fully been described in conjunction with the preferred embodiments thereof with reference to the accompanying drawings, it is to be noted that various changes and modifications are apparent to those skilled in the art. For example, either one of the inner and outer walls 13 and 14 may not always be necessary. Where the outer wall 14 is omitted, either or both of the inner wall 13 and the mouth 11 have a hardness necessary to ensure that no gap will not be formed between the inner peripheral surface of the mouth 11 and the outer peripheral surface of the inner wall 13 at the time the body of the bottle 10 is gripped and, therefore, elastically deformed. A similar notion equally applies even where the inner wall 13 is omitted.

Moreover, the size of the atomizer may be suitably selected as desired. However, a series of experiments have shown that, with the construction of FIG. 1 having the nozzle 15a of 0.7 mm. in bore size and the J-shaped tube 18 of 1.8 mm. in inner diameter and with the use of the liquid medium 19 of about 40 dyne/cm filled in the tube 18, 60 ml. or more in volume of the bottle 10 is found sufficient to atomize the liquid medium in an amount of 0.1 ml.

Accordingly, such changes and modifications are to be understood as included within the true scope of the present invention unless they depart therefrom.

What is claimed is:
1. An atomizer which comprises, in combination:
   an outer container having an opening through which the interior of said container is communicated to the atmosphere;
   a nozzle assembly including a hollow nozzle member, having a substantially elongated passage defined therein, and a body portion, said hollow nozzle member having one end formed with a nozzle in communication with said passage and the other end integrally formed with said body portion, said body portion being mounted on said outer container with said passage in communication with the interior of the container through said opening in said container;
   an inner container including a tube portion and a container portion containing a predetermined amount of liquid medium to be atomized, said tube portion having one end inserted into the passage in the nozzle member and terminating adjacent said nozzle and the other end coupled to said container portion;
   means for defining an orifice through which, when a grip is applied to the outer container forcing air within the outer container to discharge to the atmosphere through the nozzle, a stream of the air flows while creating within the tube portion a negative pressure necessary to draw the liquid medium within the container portion upwards towards the nozzle through the tube portion, and, with thus created negative pressure in concert with the positive pressure given onto the surface of the liquid medium, to drive said liquid medium towards the nozzle to be atomized;
   and wherein said inner container is comprised of a substantially J-shaped tube having a long straight portion, a substantially U-shaped portion and a short straight portion, having one end integrally connected with said long straight portion through said U-shaped portion and wherein said tube portion and said container portion of said inner container being respectively constituted by said long straight portion and said short straight and U-shaped portions of said J-shaped tube.
2. The atomizer as claimed in claim 1, wherein said outer container is comprised of a bottle made of elastically deformable material and having a mouth in communication with said opening and wherein said body portion is of double walled construction having inner and outer walls, said nozzle assembly being mounted on said mouth while the latter is engaged into an annular space defined between said inner and outer walls.

* * * * *